United States Patent [19]

Tanaka

[11] Patent Number: 5,146,003

[45] Date of Patent: Sep. 8, 1992

[54] 3-AMINO-2-HYDROXYBORNANE DERIVATIVES, ASYMMETRIC MICHAEL REACTION USING THE SAME, AND PROCESS FOR PREPARING OPTICALLY ACTIVE MUSCONE UTILIZING MICHAEL REACTION

[75] Inventor: Kazuhiko Tanaka, Kyota, Japan

[73] Assignee: Nippon Mining Co., Ltd., Tokyo, Japan

[21] Appl. No.: 623,296

[22] Filed: Dec. 6, 1990

[30] Foreign Application Priority Data

Dec. 8, 1989 [JP] Japan .................................. 1-317527
Jun. 6, 1990 [JP] Japan .................................. 2-146190

[51] Int. Cl.$^5$ .............................................. C07C 45/69
[52] U.S. Cl. .................................... 568/350; 568/347
[58] Field of Search ................................ 568/347, 350

[56] References Cited

PUBLICATIONS

Suzuki et al., Chem. Abst., vol. 143062e (1983).
The Chemical Society of Japan, Lectures (II) of the 58th Spring Meeting, Lecture No. 3 IIID 16, p. 1602 (1989).
2nd International Conference of Hetero Atomic Chemistry, Abstracts, p. 129, Lecture No. PA-44 (1989).
*Fusai Gosei To Kogaku Bunkatsu No Shinpo*, Kagaku Zokan, No. 97, pp. 44-45, Kaguku Dojin (1982).
Mookherjee et al, J. Org. Chem., vol. 36, No. 26, pp. 4124-4125 (1971).

*Primary Examiner*—James H. Reamer
*Attorney, Agent, or Firm*—Birch, Stewart, Kolasch & Birch

[57] ABSTRACT

A 3-amino-2-hydroxybornane derivative represented by formula (I):

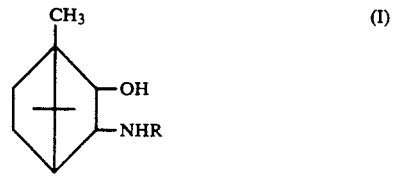

wherein R represents a furfuryl group, a 1-methylpyrrolylmethyl group, or a benzyl group, is disclosed. The compound is useful as a ligand in an asymmetric Michael reaction, particularly for the production of an optically active muscone.

16 Claims, No Drawings

3-AMINO-2-HYDROXYBORNANE DERIVATIVES, ASYMMETRIC MICHAEL REACTION USING THE SAME, AND PROCESS FOR PREPARING OPTICALLY ACTIVE MUSCONE UTILIZING MICHAEL REACTION

FIELD OF THE INVENTION

This invention relates to novel 3-amino-2-hydroxybornane derivatives, a process of an asymmetric Michael reaction using the 3-amino-2-hydroxybornane derivative as a ligand, and a process for preparing an optically active muscone utilizing the asymmetric Michael reaction.

BACKGROUND OF THE INVENTION

The present inventor previously proposed a process for converting diethylzinc to an aldehyde by an asymmetric reaction using various 3-amino-2-hydroxybornane derivatives of exo or endo form as a ligand as reported, e.g., in The Chemical Society of Japan, *Lectures (II) of the 58th Spring Meeting*, Lecture No. 3 IIID 16, p. 1602 (1989) and the 2nd International Conference of Hetero Atomic Chemistry, *Abstracts*, p. 129, Lecture No. PA-44 (1989).

3-Amino-2-hydroxybornane derivatives used in the process proposed are represented by formula:

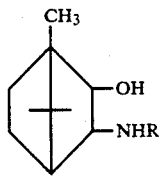

wherein R represents a methyl group, a cyclohexylmethyl group, a 1-methylpyrrolidinylmethyl group, a diphenylethyl group, or a thenyl group. A compound having the above formula wherein R represents a furfuryl group, a 1-methylpyrrolylmethyl group or a benzyl group is unknown and novel.

On the other hand, 1,4-addition to 2-cyclohexenone by an organometallic reagent using (-)-sparteine, 1,4-bis(dimethylamino)-2,3-dimethoxybutane,1,2,3,4-tetramethoxybutane,or 1,4-bis(dimethylamino)-2,3-bis(2-N,N-dimethylaminoethoxy)butane, etc. as a ligand has been reported as an asymmetric Michael reaction distinguishing the enantioface as described in *Fusai Gosei To Kogaku Bunkatsu No Shinpo*, Kagaku Zokan, No. 97, pp. 44-45, Kagaku Dojin (1982). However, there has been reported no case in which a 3-amino-2-hydroxybornane derivative is used as an asymmetric ligand.

Further, it has been proposed to synthesize muscone by reacting 2-cyclopentadecenone with a methyl Grignard reagent in the presence of cuprous chloride and diethyl ether as described in *Journal of Organic Chemistry*, Vol. 36, No. 26, pp. 4124-4125 (1971) This process, however, produces only racemic muscone.

SUMMARY OF THE INVENTION

In light of the above-described circumstances, the inventors have conducted extensive investigations. As a result, it has how been found that a 3-amino-2-hydroxybornane derivative can be used as a ligand in an asymmetric Michael reaction and that a naturally-occurring optically active muscone, e.g.., (R)-muscone, can be synthesized from 2-cyclopentadecenone by utilizing such an asymmetric Michael reaction. The present invention has been completed based on these findings.

An object of the present invention is to provide a novel compound which can be used in an asymmetric Michael reaction.

Another object of the present invention is to provide a novel ligand compound which broadens the application of an asymmetric Michael reaction.

A further object of the present invention is to provide a process for preparing an optically active muscone which utilizes the above-described reaction.

The present invention relates to a novel 3-amino-2-hydroxybornane derivative represented by formula (I):

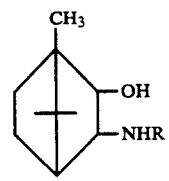

wherein R represents a furfuryl group, a 1-methylpyrrolylmethyl group, or a benzyl group.

The present invention further relates to a process of an asymmetric Michael addition reaction which comprises using a compound of exo or endo form represented by formula (II):

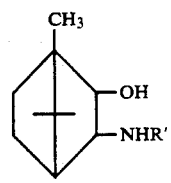

wherein R' represents a methyl group, a thenyl group, a furfuryl group, a 1-methylpyrrolylmethyl group, a benzyl group, or a 1-methylpyrrolidinylmethyl group, as a ligand.

The present invention furthermore relates to a process for preparing an optically active muscone which comprises subjecting 2-cyclopentadecenone to an asymmetric Michael reaction in the presence- of a compound of exo or endo form represented by formula (II) and, more particularly, in a diethyl ether .solvent or a mixed solvent of toluene and tetrahydrofuran in the presence of endo-2-hydroxy-endo-3-[(1-methyl-2-pyrrolyl)methylamino]bornane or (1S,2S,3R,4R)-endo-2-hydroxy-endo-3-[(1-methyl-2-pyrrolyl)methylamino]bornane.

DETAILED DESCRIPTION OF THE INVENTION

Typical examples of the compounds represented by formula (I) and their physicochemical properties are shown below.

Exo-3-furfurylamino-exo-2-hydroxybornane:

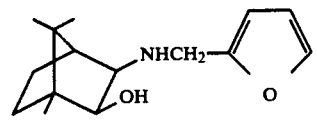

IR (KBr, cm$^{-1}$): 3100, 2920, 1455, 1115, 760

¹H-NMR (CDCl₃, ppm): 0.76, 0.94, 1.04 (s, 11 H), 1.10 −1.88 (m, 4 H), 2.75 (d, J=10 Hz, 1H), 3.40 (d, J=10 Hz, 1H), 3.74 (s, 2 H), 4.32 (brs, 1 H), 6.28 (m, 2 H), 7.36 (m, 1H)

Melting Point: 100° C.

Elemental Analysis (calcd.): C:72.25%; H: 9.30%; O:12.83%; N: 5.62% .

$[\alpha]_D^{23}$: (c 1.95; CHCl₃): +42.9°.

Endo-3-furfurylamino-endo-2-hydroxybornane:

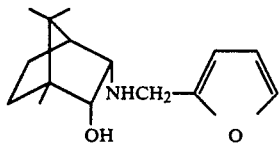

IR (KBr, cm⁻¹): 2925, 1160, 765, 755.

¹H-NMR (CDCl₃, ppm): 0.90 (s, 9 H), 1.10-1.62 (m, 4 H), 1.62-1.96 (m, 2 H), 3.24 (dt, J=12, 6 Hz, 1 H), 3.59 (m, 4 H), 6.28 (d, J=4 Hz, 1H), 6.44 (m, 1 H), 7.49 (s, 1H).

Melting Point: 71° C.

Elemental Analysis (calcd.): C: 72.25%; H: 9.30%; O:12.83%; N: 5.62%

$[\alpha]_D^{23}$(c 2.19; CHCl₃):+11.3°.

Exo-2-hydroxy-exo-3-[(1-methyl-2-pyrrolyl)methylamino]bornane:

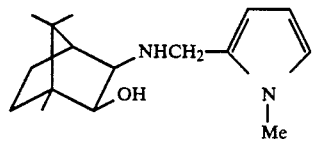

IR (KBr, cm⁻¹): 3100, 2950, 1500, 1110, 730.

¹H-NMR (CDCl₃, ppm): 0.74, 0.92, 1.00 (s, 11H), 1.16 (s, 1H), 1.10 1.88 (m, 3 H), 2.76 (d, J=8 Hz, 1H), 3.36 (d, J=8 Hz, 1H), 3.52 (s, 4 H), 3.66 (m, 2 H), 6.00 (m, 2 H), 6.56 (m, 1H).

Melting Point: 103° C.

Elemental Analysis (calcd.): C:73.24%; H:9.99%; O:6.10%; N: 10.68%

$[\alpha]_D^{21}$(c 2.12; CHCl₃)+36.4°.

Endo-2-hydroxy-endo-3-[(1-methyl-2-pyrrolyl)methylamino]-bornane:

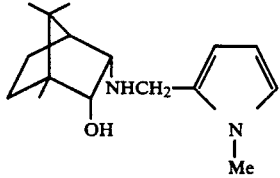

IR (KBr, cm⁻¹): 3100, 2940, 1500, 1110, 730.

¹H-NMR (CDCl₃, ppm): 0.94 (s, 9 H), 1.08-1.60 (m, 4 H), 1.60-1.92 (m, 2 H), 3.26 (q, J=12 Hz, 1 H), 3.70 (m, 7 H), 6.12 (m, 2 H), 6.70 (t, J=3 Hz, 1 H)

Melting Point: 82.5° C.

Elemental Analysis (calcd.): C:73.24%; H:9.99%; O:6.10%; N:10.68% .

$[\alpha]_D^{26}$(c 1.95, CHC₃):+18.6°.

Exo-3-benzylamino-exo-2-hydroxybornane:

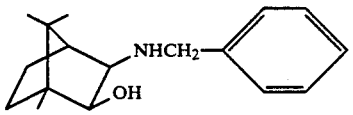

IR (KBr, cm⁻¹):3370, 2870, 1450.

¹H-NMR (CDCl₃, ppm): .76 (s, 3 H), 0.95-1.00 (m, 4 H), 1.04 (s, 3 H), 1.20-2.04 (m, 5 H), 2.81 (d, J=8.0 Hz, 1 H), 3.50 (d, J=8.0 Hz, 1H), 3.85 (s, 2 H), 7.36 (s, 5 H).

Melting Point: 88.5° C.

Elemental Analysis (calcd.): C: 78.72%; H:9.72%; O:6.16%; N:5.40%

$[\alpha]_D^{23}$(c 2.03; CHCl₃):+22.4°.

Endo-3-benzylamino-endo-2-hydroxybornane:

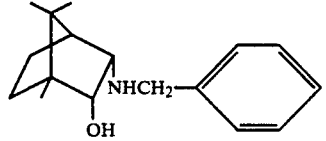

IR (KBr, cm⁻¹):3265, 2905, 1450, 1070, 740.

¹H-NMR (CDCl₃, ppm):0.85 (m, 10 H), 1.00-1.80 (m, 5 H), 2.60 (m, 2 H), 3.20 (m, 1H), 3.68 (m, 2 H), 7.26 (m, 5 H)

Melting Point: 65° C.

Elemental Analysis (calcd.): C:78.72%; H:9.72%; O:6.16%; N: 5.40%

$[\alpha]_D^{24}$ (c 2.03, CHCl₃):+27.9°.

(1S, 2S, 3R, 4R)-Endo-2-hydroxy-endo-3-[(1-methyl-2-pyrrolyl)-methylamino]bornane:

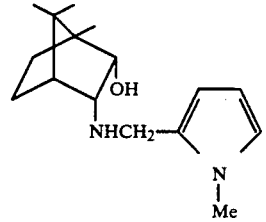

IR (KBr, cm⁻¹):3100, 2942, 1502, 1112, 732

¹H-NMR (CDCl₃, ppm):0 94 (s, 9 H), 1.08-1.60 (m, 4 H), 1.60-1.92 (m, 2 H), 3.26 (q, J=12 Hz, 1 H), 3.70 (m, 7 H), 6.12 (m, 2 H), 6.70 (t, J=3 Hz, 1H).

Melting Point: 82° C.

Elemental Analysis (calcd.): C:73.24%; H:9.99%; O:6.10%; N: 10.68%

$[\alpha]_D^{21}$ (c 1.95, CHCl₃):−18.3°.

SYNTHESIS

These compounds can be synthesized as follows. D-camphor or L-camphor is reacted with isoamyl nitrite in the presence of metallic sodium, and the product is reduced with lithium aluminum hydride to obtain 3-amino-2-hydroxybornane. The resulting 3-amino-2-hydroxybornane is reacted with furoyl chloride, 2-thiophenecarbonyl chloride-, or benzoyl chloride in the presence of pyridine or 4-dimethylaminopyridine, or it is subjected to a dehydrating reaction with furfural, 1-methyl-2-pyrrolecarbaldehyde, 1-benzyloxycarbonyl-L-proline, or benzaldehyde in the presence of a dehydrating agent. The resulting product is then reduced with lithium aluminum hydride to obtain a 3-amino-2-hydroxybornane derivative of exo or endo form.

The asymmetric Michael reaction to which the present invention is applicable is an asymmetric 1,4-addition reaction to a prochiral α,β-unsaturated ketone with an achiral organometallic reagent. The present invention is particularly advantageous for a Michael reaction distinguishing the enantioface of an α,β-unsaturated ketone.

Commonly employed achiral organometallic reagents including Grignard reagents and an alkyl lithium, can be used in the Michael reaction. The prochiral α,β-unsaturated ketone includes various α,β-unsaturated ketones generally used in a Michael reaction. In particular, an optically active muscone useful as a perfume can be obtained by using 2-cyclopentadecenone as an α,β-unsaturated ketone. The α,β-unsaturated ketone is preferably used in a substantially theoretical amount with respect to the organometallic reagent and is appropriately selected from the range of from 0.1 to 10 times the equivalent according to the kind of the reagent.

In the asymmetric Michael reaction according to the present invention, the compounds represented by formula (II) having an exo or endo form are used as an asymmetric ligand. The ligand functions, in the co-presence of the above-described achiral organometallic reagent, to not only improve the chemical stability of the reagent but bring such that a complex formed by bonding therebetween causes a selective 1,4-addition reaction to the α,β-unsaturated ketone to promote the reaction distinguishing the enantioface. That is, the ligand forms a chiral environment. Specific examples of the compounds of formula (II) include the above-enumerated novel compounds and, in addition, endo-2-hydroxy-endo-3-(thenylamino)bornane, exo-2-hydroxy-exo-3-(thenylamino)bornane, endo-2-hydroxy-endo-3-(methylamino)bornane, exo-2-hydroxy-exo-3-(methylamino)bornane, endo-2-hydroxy-endo-3-[[(S)-1-methyl-2-pyrrolidinyl]methylamino]bornane, and exo-2-hydroxy-exo-3-[[(S)-1-methyl-2pyrrolidinyl]methylamino]bornane. These ligands are preferably used in an amount of at least 0.1 molar equivalent, and more preferably from 1 to 10 molar equivalents, based on the α,β-unsaturated ketone.

The asymmetric Michael reaction can be carried out at a temperature ranging from −100° to 100° C. The lower the temperature, the higher the stereoselectivity. In order to increase positional selectivity, a catalyst is preferably used. Suitable catalysts include those used in general Michael reactions, e.g., cuprous iodide, cuprous cyanide, cuprous thiocyanate, and cuprous bromide.

In a preferred embodiment of the asymmetric Michael reaction according to the present invention, 2-cyclopentadecenone is subjected to an asymmetric Michael reaction in diethyl ether or a mixed solvent of toluene and tetrahydrofuran as a reaction solvent by using endo-2-hydroxy-endo-3-[(1-methyl-2pyrrolyl)methylamino]bornane as an asymmetric ligand. In this embodiment, (R)-form 3-methylcyclopentadecanone, so-called natural muscone, can be obtained at an optical purity of 100% or nearly 100%. The diethyl ether to be used as a solvent is preferably dried diethyl ether. The toluene/tetrahydrofuran mixed solvent preferably has a mixing ratio of 110:1 to 10:1 by volume. If the toluene to tetrahydrofuran mixing ratio is out of the above range, that is, if the amount of either toluene or tetrahydrofuran is too large, it follows that the optical purity and yield of muscone will be reduced.

The present invention is now illustrated in greater detail with reference to the following Synthesis Examples and Examples, but it should be understood that the present invention is not deemed to be limited thereto. All the percents are by weight unless otherwise specified.

SYNTHESIS EXAMPLE 1

Synthesis of Exo-3-amino-exo-2-hydroxybornane

In 600 ml of dried diethyl ether was dissolved 130 g (0.854 mol) of commercially available D-camphor, and 20.4 g of metallic sodium was added thereto. The solution was kept at 0° C. with stirring, and 123 ml (0.916 mol) of isoamyl nitrite was added thereto to conduct a reaction for 14 hours. After completion of the reaction, 200 ml of water was added to the reaction mixture, and the aqueous layer was separated. To the aqueous layer was added 400 ml of 10% hydrochloric acid, and the solid thus formed was extracted with diethyl ether. The ether layer was dried and concentrated to obtain 51 g of 3-hydroxyiminocamphor.

To 700 ml of diethyl ether was added 21 g of lithium aluminum hydride in an argon stream, and a solution of 30 g of the above-prepared 3-hydroxyiminocamphor in 260 ml of dried diethyl ether was added thereto dropwise to conduct reduction at 25° C. for 16 hours. After completion of the reduction reaction, 21 ml of water, a 15% sodium hydroxide aqueous solution, and then 63 ml of water were successively added thereto. The resulting mixture was filtered by using a high flow super cell, and the filtrate was extracted with 10% hydrochloric acid. The hydrochloric acid aqueous solution was made alkaline with a 15% sodium hydroxide aqueous solution and then extracted with diethyl ether to obtain 22.4 g of crude exo-3-amino-exo-2-hydroxybornane. The resulting crude product was dissolved in 19.3 ml of diethyl carbonate and allowed to react at 150° C. for 6 hours to obtain an oxazolidinone, which was then recrystallized from a mixed solvent of hexane and ethyl acetate (2:1 by volume). The resulting crystal was dissolved in 70 ml of a 12% sodium hydroxide aqueous solution, and 100 ml of ethanol was added to the solution, followed by hydrolysis under heating. The hydrolysate was extracted with diethyl ether, and the ether layer was dried and concentrated to obtain 6.39 g of exo-3-amino-exo-2-hydroxybornane as a white crystal.

SYNTHESIS EXAMPLE 2

Synthesis of Endo-3-amino-endo-2-hydroxybornane

In 300 ml of a 15% sodium hydroxide aqueous solution was dissolved 36.4 g of the 3-hydroxyiminocamphor obtained in Synthesis Example 1, and 43.7 g of metallic zinc was added to the solution in small portions to conduct reduction. After completion of the reduction reaction, the reaction mixture was extracted with diethyl ether, and the ether layer was dried and concentrated to obtain 16.6 g of crude endo-3-aminocamphor.

To 85 ml of dried diethyl ether was added 21.8 g of an aluminum trichloride powder at 15° C or a lower temperature, and 2.07 g of lithium aluminum hydride was added thereto to prepare dichloroaluminum hydride. A solution of 16.6 g of the above-prepared crude endo-3-aminocamphor in 80 ml of dried diethyl ether was added thereto to conduct reduction. The reaction mixture was decomposed by addition of 198 ml of water and 82 ml of a 28% sodium hydroxide aqueous solution and extracted with diethyl ether to obtain 5.67 g of endo-3-amino-endo-2-hydroxybornane as a white crystal.

SYNTHESIS EXAMPLE 3

Synthesis of Exo-3-furfurylamino-exo-2-hydroxybornane

In 60 ml of tetrahydrofuran was dissolved 3.89 g (0.023 mol) of exo-3-amino-exo-2-hydroxybornane prepared in Synthesis Example 1. To the solution was added 1.1 equivalent of 4-dimethylaminopyridine, and the solution was kept at 0° C. A solution of 3.00 g (0.023 mol) of furoyl chloride in 10 ml of tetrahydrofuran was added thereto dropwise, followed by stirring at 0° C. for 1 hour and then at room temperature overnight. After completion of the reaction, the reaction mixture was poured into water and extracted with methylene chloride. The methylene chloride layer was washed successively with diluted hydrochloric acid and water and dried over sodium sulfate. The methylene chloride was removed by distillation, and the resulting solid crystal was recrystallized from hexaneethyl acetate (1:1 by volume). To 50 ml of tetrahydrofuran was added 1.63 g (3.eq.) of lithium aluminum hydride in an argon atmosphere, and a solution of 3.76 g (0.0143 mol) of the above-obtained crystal in 50 ml of tetrahydrofuran was added thereto dropwise at room temperature, followed by heating at reflux for 20 hours. The reaction product was separated by silica gel column chromatography using hexane and ethyl acetate (1:1 by volume) as an eluent, the solvent was removed by distillation, and the residue was recrystallized from hexane to obtain 2.20 g of exo-3-furfurylamino-exo-2-hydroxybornane having the above-described physicochemical properties. The measured values of the elemental analysis were C: 72.01% H: 9.10%; and N: 5.32%, which agreed very closely with the theoretical values.

SYNTHESIS EXAMPLE 4

Synthesis of Endo-3-furfurylamino-endo-2-hydroxybornane

In 100 ml of tetrahydrofuran was dissolved 7.91 g (0.047 mol) of endo-3-amino-endo-2-hydroxybornane obtained in Synthesis Example 2, and 1.1 equivalent of 4-dimethylaminopyridine was added thereto. In 15 ml of tetrahydrofuran was dissolved 6.10 g (0.047 mol) of furoyl chloride at room temperature, and the resulting solution was added dropwise to the mixture at 0° C., followed by stirring at room temperature overnight. The precipitated crystal was collected. To 160 ml of tetrahydrofuran was added 4.14 g (3 eq.) of lithium aluminum hydride in an argon atmosphere, and a solution of 9.56 g of the collected crystal in 160 ml of tetrahydrofuran was added thereto dropwise at room temperature. After the dropwise addition, the reaction mixture was heated at reflux for 14 hours. The resulting reaction product was separated by silica gel column chromatography using hexane/ethyl acetate (1:1 by volume) as an eluent. The solvent was removed by distillation, and the residue was recrystallized from hexane to obtain 3.70 g of endo-3-furfurylamino-endo-2-hydroxybornane having the abovedescribed physicochemical properties. The measured values of the elemental analysis were C: 72.24%; H: 9.42%; N: 5.65%, which agreed very closely with the theoretical values.

SYNTHESIS EXAMPLE 5

Synthesis of Exo-2-hydroxy-exo-3-[(1-methyl-2-pyrrolyl)methylamino]bornane

In 45 ml of benzene was dissolved .3.94 g (0.0233 mol) of exo-3-amino-2-exo-2-hydroxybornane obtained in Synthesis Example 1, and 9.93 g (3 eq.) of anhydrous sodium sulfate and 2.54 g (0.0233 mol) of 1-methyl-2-pyrrolecarbaldehyde were added thereto, followed by allowing the mixture to react at room temperature for 4 days under stirring. The reaction mixture was filtered, the solvent was removed under reduced pressure, and the residue was dried using a vacuum pump to obtain a solid. To 100 ml of diethyl ether was added 1.77 g of lithium aluminum hydride in an argon stream, and to the solution was added dropwise a solution of the above-collected solid in 90 ml of diethyl ether at room temperature. After the dropwise addition, the reaction mixture was heat-refluxed for 3 hours. The reaction product was separated by silica gel column chromatography using hexane/ethyl acetate (1:1 by volume) as an eluent, the solvent was removed by distillation, and the residue was recrystallized from hexane to obtain 3.09 g of exo-2-hydroxy-exo-3-[(1-methyl-2-pyrrolyl)methylamino]bornane having the above-described physicochemical properties. The measured values of the elemental analysis were C: 73.09%; H: 9.82%; N: 10.65%, which agreed very closely with the theoretical values.

SYNTHESIS EXAMPLE 6

Synthesis of Endo-2-hydroxy-endo-3-[(1-methyl-2-pyrrolyl)methylamino]bornane

The titled compound having the above-described physicochemical properties was obtained in the same manner as in Synthesis Example 5, except that exo-3-amino-exo-2-hydroxybornane was replaced with endo-3-amino-endo-2-hydroxybornane. The measured values of the elemental analysis on the compound were C: 73.10%; H: 9.99%; and N: 10.69%, which agreed very closely with the theoretical values.

SYNTHESIS EXAMPLE 7

Synthesis of Exo-3-benzylamino-exo-2-hydroxybornane

The titled compound having the above-described physicochemical properties was obtained in the same manner as in Synthesis Example 5, except that 1-methyl-2-pyrrolecarbaldehyde was replaced with benzaldehyde. The measured values of the elemental analysis were C:78.53%; H:9.51%; and N:5.20%, which agreed very closely with the theoretical values.

SYNTHESIS EXAMPLE 8

Synthesis of Endo-3-benzylamino-endo-2-hydroxybornane

The titled compound having the above-described physicochemical properties was obtained in the same manner as in Synthesis Example 4, except for replacing furoyl chloride with benzoyl chloride. The measured values of the elemental analysis were C:78.84%; H:9.99%; and N:5.62%, which agreed very closely with the theoretical values.

SYNTHESIS EXAMPLE 9

Synthesis of (1S,2S,3R,4R)-Endo-2-hydroxy endo-3-[(1-methyl-2-pyrrolyl)methylamino]bornane The titled compound having the above-described physicochemical properties was obtained in the same manner as in Synthesis Example 6, except that the endo-3-amino-endo-2-hydroxybornane obtained from D-camphor was replaced with (1S,2S,3R,4R)-endo-3-amino-endo-2-hydroxybornane obtained from L-camphor. The measured values of the elemental analysis were C:73.11%; H:10.01%; and N:10.71%, which agreed very closely with the theoretical values.

EXAMPLES 1 TO 12

An asymmetric Michael reaction of 2-cyclopentadecenone was carried out by using each of the 3-amino-2-hydroxybornane derivatives shown in Table 1 below as a ligand as follows.

In 30 ml of toluene was dissolved 3.56 mmol, 1.62 mmol, 3.86 mmol, or 1.94 mmol of a ligand, and the solution was cooled to 0° C. To the solution was added 7.4 ml of a 0.97M diethyl ether solution of methyl lithium (7.12 mmol), followed by stirring at room temperature for 30 minutes. After cooling the reaction mixture to −30° C, 0.339 g (1.78 mmol) of cuprous iodide was added thereto, followed by stirring at −30° to −20° C. for 1 hour. The reaction mixture was cooled to −78° C., and 3.7 ml of a 0.97M diethyl ether solution of methyl lithium (3.56 mmol) was further added thereto, followed by stirring at −78° C. for 30 minutes. The reaction mixture was then heated up to −25° C. over a period of 90 minutes.

The solution was cooled to −78° C., and a solution of 0.3604 g (1.62 mmol) of 2-cyclopentadecenone in 1 ml of toluene was added thereto dropwise, followed by stirring at −78° C. for 17 hours. To the reaction mixture was added 4 ml of a 1:1 (by volume) mixture of aqueous ammonia and a saturated ammonium chloride aqueous solution, followed by heating up to room temperature. The aqueous layer was removed, and the organic layer was washed successively with a 1:1 (by volume) mixture of aqueous ammonia and a saturated ammonium chloride aqueous solution, a 5% hydrochloric acid aqueous solution, a saturated sodium chloride aqueous solution, and a saturated sodium carbonate aqueous solution, and dried over sodium sulfate. The toluene was removed by distillation, and the residue was purified by silica gel column chromatography using hexane/ethyl acetate (40:1 by volume) as an eluent and then distilled under reduced pressure to obtain an optically active muscone. The yield, optical rotation, optical purity, and stereochemistry of the product were determined, and the results obtained are shown in Table 1.

TABLE 1

| Example No. | Ligand | Amount of Ligand (mmol) | Optical Rotation [(°C., MeOH Conc.)] | Optical Purity (% ee) | Stereo-chemistry | Chemical Yield* (mol %) |
|---|---|---|---|---|---|---|
| 1 | Exo-2-hydroxy-exo-3-(thenyl-amino)bornane | 3.56 | +5.74 (25, 5.02) | 49 | S | 82 |
| 2 | Exo-2-hydroxy-exo-3-(thenyl-amino)bornane | 1.62 | +3.65 (23, 5.15) | 31 | S | 97 |
| 3 | Endo-2-hydroxy-endo-3-(thenyl-amino)bornane | 3.56 | −1.38 (22, 3.46) | 12 | R | 36 |
| 4 | Exo-3-furfurylamino-exo-2-hydroxybornane | " | +5.83 (24, 5.15) | 50 | S | 86 |
| 5 | Endo-3-furfurylamino-endo-2-hydroxybornane | " | +4.10 (23, 5.06) | 35 | S | 82 |
| 6 | Exo-2-hydroxy-exo-3-[(1-methyl-2-pyrrolyl)methylamino]bornane | " | +6.69 (25, 5.17) | 57 | S | 88 |
| 7 | Endo-2-hydroxy-endo-3-[(1-methyl-2-pyrrolyl)methylamino]bornane | " | +1.12 (24, 5.17) | 10 | S | 88 |
| 8 | Exo-3-benzylamino-exo-2-hydroxy-bornane | " | +4.54 (27, 5.25) | 39 | S | 72 |
| 9 | Endo-2-hydroxy-endo-3-(methyl-amino)bornane | 3.86 | −4.54 (24, 5.36) | 39 | S | 70 |
| 10 | Endo-2-hydroxy-endo-3-(methyl-amino)bornane | 1.94 | −2.73 (23, 5.01) | 23 | R | 84 |
| 11 | Exo-2-hydroxy-exo-3-[[(S)-1-methyl-2-pyrrolidyl]methylamino]bornane | " | +3.02 (22, 1.10) | 26 | S | 93 |
| 12 | Endo-2-hydroxy-endo-3-[[(S)-1-methyl-2-pyrrolidyl]methylamino]bornane | " | −2.43 (25, 5.46) | 21 | R | 72 |

*The chemical yield is based on the theoretical value.

EXAMPLE 13

In 30 ml of toluene was dissolved 3.56 mmol of endo-2-hydroxy-endo-3-[(1-methyl-2-pyrrolyl)methylamino]bornane, and 3.8 ml of a 0.97M diethyl ether solution of methyl lithium (3.57 mmol) was added thereto, followed by stirring at room temperature for 30 minutes. The solution was cooled to −20° C., and 0.339 g (1.78 mmol) of cuprous iodide was added thereto. The mixture was stirred for about 4 hours until the temperature rose to 0° C. After cooling the reaction mixture to −78° C., 3.8 ml of a 0.97M diethyl ether solution of methyl lithium (3.57 mmol) was further added thereto, and the mixture was stirred at −78° C. for 30 minutes, followed by heating to −25° C. over about 1 hour.

Thereafter, the same procedures as in Examples 1 to 12 were followed to obtain muscone in a yield of .70 mol %. The resulting compound was R-form having an optical rotation of −10.41° (at 22° C., c 5.05, MeOH) and an optical purity of 89 %ee.

EXAMPLE 14

In 90 ml of dried diethyl ether was dissolved 11 mmol of endo-2-hydroxy-endo-3-[(1-methyl-2-pyrrolyl)methylamino]bornane in an argon stream, and 11 mmol of methyl lithium was added thereto at 0° C., followed by stirring for 1 hour. After cooling the solution to −25° C., 5.5 mmol of cuprous iodide was added, and the mixture was heated to −5° C. over 2 hours, followed by cooling to −78° C. To the mixture was further added 11 mmol of methyl lithium, followed by stirring for 30 minutes. The reaction mixture was heated from −78° to −5° C. over 2 hours and then cooled again to −78° C.

In 10 ml of dried diethyl ether was dissolved 5 mmol of (E)-2-cyclopentadecenone, and the solution was added dropwise to the above solution at −78° C. The mixture was allowed to react at that temperature for 15 hours, and 12 ml of a 1:1 (by volume) mixture of aqueous ammonia and a saturated ammonium chloride aqueous solution was added thereto. The reaction mixture was extracted with diethyl ether, and the extracted product was purified by silica gel column chromatography using hexane/ethyl acetate (45:1 by volume) to obtain muscone in a chemical yield of 57 mol %. The resulting muscone was R-form having an optical rotation of −11.6° (at 21° C., c 5.03, MeOH) and an optical purity of 99%ee.

EXAMPLE 15

In 90 ml of dried toluene was dissolved 11 mmol of endo-2-hydroxy-endo-3-[(1-methyl-2-pyrrolyl)methylamino]bornane in an argon stream, and 11 mmol of methyl lithium was added thereto at 0° C., followed by stirring for 1 hour. After cooling to −25° C., 5.5 mmol of cuprous iodide was added thereto, and the temperature was raised from −25° C. to −6° C. over 2.5 hours. The reaction mixture was cooled to −78° C, and 11 mmol of methyl lithium was further added thereto, followed by stirring for 30 minutes. The reaction mixture was heated from −78° C. to −5° C. over 2 hours and then cooled again to −78° C. To the solution was added 0.82 ml of dried tetrahydrofuran, followed by stirring at −78° C. for 15 minutes.

In 10 ml of dried toluene was dissolved 5 mmol of (E)-2-cyclopentadecenone, and the solution was added dropwise to the above solution, followed by allowing the reaction to proceed at a temperature from −78° C. to −60° C. for 15 hours. Thereafter, the same procedures as in Example 14 were followed to obtain muscone in a chemical yield of 89 mol %. The resulting muscone was R-form having an optical rotation of −12.0° (at 21° C., c 5.07, MeOH) and an optical purity of 100%ee.

EXAMPLE 16

The same procedures as in Example 15 were repeated, except for changing the amount of dried tetrahydrofuran added from 0.82 ml to 1.63 ml. As a result, muscone of R-form having an optical rotation of −11.5° (at 23° C., c 5.13., MeOH) and an optical purity of 99 %ee was obtained in a chemical yield of 94 mol %.

When the amount of dried tetrahydrofuran added was changed to 30 ml, the chemical yield was 21 mol %, and the optical purity was 81 %ee.

EXAMPLE 17

In 90 ml of dried toluene was dissolved in an argon stream 11 mmol of (1S,2S,3R,4R)-endo-2-hydroxy-endo-3-[(1-methyl-2pyrrolyl)methylamino]bornane synthesized from L-camphor, and 11 mmol of methyl lithium was added thereto at 0° C., followed by stirring for 1 hour. The solution was cooled to −25° C., and 5.5 mmol of cuprous iodide was added thereto, followed by elevating the temperature from −25° C. to −6° C. over 2.5 hours. After cooling the solution to −78° C., 11 mmol of methyl lithium was further added thereto, followed by stirring for 30 minutes. The reaction solution was heated from −78° C. to −5° C. over 2 hours and then cooled again to −78° C. To the solution was added 0.82 ml of dried tetrahydrofuran, followed to stirring at −78° C. for 15 minutes.

In 10 ml of dried toluene was dissolved 5 mmol of (E)-2-cyclopentadecenone, and the solution was added dropwise to the above solution, followed by allowing the reaction to proceed at −78° C. to −60° C. for 15 hours. Thereafter, the same procedures as in Example 14 were followed to obtain muscone having an optical rotation of +11.8° (at 21° C., c 5.13, MeOH) and an optical purity of 100 %ee in a chemical yield of 90 mol %.

As described above, the novel 3-amino-2-hydroxybornane derivatives according to the present invention can be used in an asymmetric Michael reaction. Use of the ligand as proposed in the present invention broadens the range of application of an asymmetric Michael reaction, making it possible to synthesize various optically active compounds and further to prepare an optically active muscone excellent as a perfume.

While the invention has been described in detail and with reference to specific examples thereof, it will be apparent to one skilled in the art that various changes and modifications can be made therein without departing from the spirit and scope thereof.

What is claimed is:

1. A process for carrying out an asymmetric Michael addition reaction which comprises an asymmetric 1,4-addition reaction of an achiral organometallic reagent to a prochiral α,β-unsaturated ketone in the presence of a compound of exo or endo form represented by formula (II):

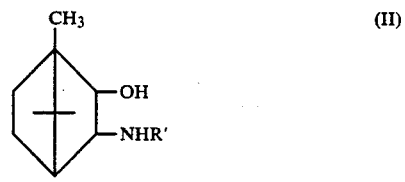

wherein R' represents a methyl group, a thienyl group, a furfuryl group, a 1-methylpyrrolylmethyl group, a benzyl group, or a 1-methylpyrrolidinylmethyl group.

2. A process for preparing an optically active muscone which comprises subjecting 2-cyclopentadecenone to an asymmetric Michael reaction in the presence of a compound of exo or endo form represented by formula (II):

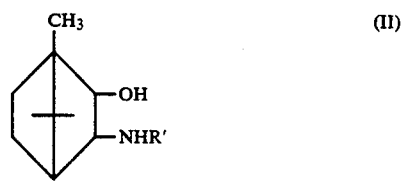

wherein R' represents a methyl group, a thenyl group, a furfuryl group, a 1-methylpyrrolylmethyl group, a benzyl group, or a 1-methylpyrrolidinylmethyl group.

3. A process for preparing (R)-muscone which comprises subjecting 2-cyclopentadecenone to an asymmetric Michael reaction in a diethyl ether solvent or a mixed solvent of toluene and tetrahydrofuran in the presence of endo-2-hydroxy-endo-3-[(1-methyl-2-pyrrolyl)methylamino]bornane.

4. A process as claimed in claim 3, wherein said mixed solvent has a toluene to tetrahydrofuran mixing ratio of from 110:1 to 10:1 by volume.

5. A process for preparing (S)-muscone which comprises subjecting 2-cyclopentadecenone to an asymmetric Michael reaction in a diethyl ether solvent or a mixed solvent of toluene and tetrahydrofuran in the presence of (1S,2S,3R,4R)-endo-2-hydroxy-endo-3-[(1-methyl-2-pyrrolyl)methylamino]-bornane.

6. A process as claimed in claim 5, wherein said mixed solvent has a toluene to tetrahydrofuran mixing ratio of from 110:1 to 10:1 by volume.

7. The process according to claim 1, wherein said achiral organometallic reagent is a Grignard reagent or an alkyl lithium.

8. The process according to claim 7, wherein said alkyl lithium is methyl lithium.

9. The process according to claim 2, wherein said Michael addition reaction uses methyl lithium as a reactant.

10. The process according to claim 2, wherein said reaction is carried out in the presence of diethyl ether or a mixture of toluene and tetrahydrofuran, as the solvent.

11. An asymmetric Michael addition reaction process comprising reacting an α,β-unsaturated ketone with an achiral organometallic reagent in the presence of a compound represented by the formula (II):

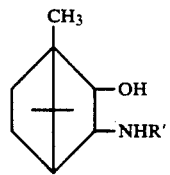

wherein $R^1$ represents a methyl group, a thienyl group, a furfuryl group, a 1-methylpyrrolylmethyl group, a benzyl group, or a 1-methylpyrrolidinylmethyl group, in endo- or exo- form.

12. The process according to claim 11, wherein said α,β-unsaturated ketone is 2-cyclopentadecenone.

13. The process according to claim 12, wherein said organometallic reagent is selected from the group consisting of a Grignard reagent and alkyl lithium.

14. The process according to claim 13, wherein said organometallic reagent is methyl lithium.

15. The process according to claim 11, wherein said addition reaction is carried out in a solvent selected from the group consisting of diethyl ether and a toluene/tetrahydrofuran mixture.

16. A process for preparing (R)-muscone which comprises subjecting 2-cyclopentadecenone and methyl lithium to an asymmetric Michael reaction in a diethyl ether solvent or a mixed solvent of toluene and tetrahydrofuran in the presence of endo-2-hydroxy-endo-3-((1-methyl-2-pyrrolyl)methylamino)bornane.

* * * * *

UNITED STATES PATENT AND TRADEMARK OFFICE
CERTIFICATE OF CORRECTION

PATENT NO. : 5,146,003
DATED : September 8, 1992
INVENTOR(S) : Kazuhiko Tanaka It is certified that error appears in the above-identified patent and that said Letters Patent is hereby corrected as shown below:

On the title page:

Under [75] Inventor, please change inventor's address from "Kyota" to --Kyoto--

Signed and Sealed this

Fourteenth Day of September, 1993

Attest:

BRUCE LEHMAN

*Attesting Officer*     *Commissioner of Patents and Trademarks*